United States Patent [19]

Butter et al.

[11] E Patent Number: Re. 31,919

[45] Reissued Date of Patent: Jun. 18, 1985

[54] AROMATICS PROCESSING CATALYSTS

[75] Inventors: Stephen A. Butter; Arthur W. Chester, both of Cherry Hill, N.J.

[73] Assignee: Mobil Oil Corporation, New York, N.Y.

[21] Appl. No.: 526,257

[22] Filed: Aug. 25, 1983

Related U.S. Patent Documents

Reissue of:

[64] Patent No.: 4,312,790
Issued: Jan. 26, 1982
Appl. No.: 140,343
Filed: Apr. 14, 1980

[51] Int. Cl.[3] ..... B01J 29/32

[52] U.S. Cl. ..... 502/66; 502/71; 502/77

[58] Field of Search ..... 252/455 Z; 585/481; 502/66, 71, 74, 77

[56] References Cited

U.S. PATENT DOCUMENTS 3,702,886 11/1972 Argauer et al. ..... 252/455 Z
3,766,056 10/1973 Young ..... 208/111

*Primary Examiner*—Carl F. Dees
*Attorney, Agent, or Firm*—A. J. McKillop; M. G. Gilman; L. G. Wise

[57] ABSTRACT

A method of preparing aromatics processing catalysts which comprises incorporating a noble metal with a member or members of a useful class of zeolites, with such incorporation occurring after zeolite crystallization, but prior to final catalyst particle formation, i.e. extrusion into particles. Said useful class of zeolites is characterized by a silica to alumina mole ratio of at least 12 and a Constraint Index in the approximate range of 1 to 12.

31 Claims, No Drawings

AROMATICS PROCESSING CATALYSTS

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to novel methods of preparing an aromatics processing catalyst, the catalyst itself, and the use of said catalyst in the processing of aromatics, particularly in xylene isomerization.

2. Description of the Prior Art

Since the announcement of the first commercial installation of Octafining in Japan in June, 1958, this process has been widely installed for the supply of p-xylene. See "Advances in Petroleum Chemistry and Refining" volume 4 page 433 (Interscience Publishers, New York, 1961). That demand for p-xylene has increased at remarkable rates, particularly because of the demand for terephthalic acid to be used in the manufacture of polyesters.

Typically, p-xylene is derived from mixtures of $C_8$ aromatics separated from such raw materials as petroleum naphthas, particularly reformates, usually by selective solvent extraction. The $C_8$ aromatics in such mixtures and their properties are as follows:

| | Freezing Point °F. | Boiling Point °F. | Density lbs./U.S. Gal. | |
|---|---|---|---|---|
| Ethylbenzene | −139.0 (−95° C.) | 277.1 (136.2° C.) | 7.26 | (871.2 g/liter) |
| P—xylene | 55.9 ( 13.3° C.) | 281.0 (138.3° C.) | 7.21 | (865.2 g/liter) |
| M—xylene | −54.2 (−47.9° C.) | 282.4 (139.1° C.) | 7.23 | (867.6 g/liter) |
| O—xylene | −13.3 (−25.2° C.) | 292.0 (144.4° C.) | 7.37 | (884.4 g/liter) |

Principal sources are catalytically reformed naphthas and pyrolysis distillates. The $C_8$ aromatic fractions from these sources vary quite widely in composition but will usually be in the range of 10 to 32 wt. % ethylbenzene with the balance, xylenes, being divided approximately 50 wt. % meta, and 25 wt. % each of para and ortho.

Individual isomer products may be separated from the naturally occurring mixtures by appropriate physical methods. Ethylbenzene may be separated by fractional distillation although this is a costly operation. Ortho xylene may be separated by fractional distillation and is so produced commercially. Paraxylene is separated from the mixed isomers by fractional crystallization.

As commercial use of para- and orthoxylene has increased there has been interest in isomerizing the other $C_8$ aromatics toward an equilibrium mix and thus increasing yields of the desired xylenes. At present, several xylene isomerization processes are available and in commercial use.

The isomerization process operates in conjunction with the product xylene separation processes. A virgin $C_8$ aromatics mixture is fed to such a processing combination in which the residual isomers emerging from the product separation steps are then charged to the isomerizer unit and the effluent isomerizate $C_8$ aromatics are recycled to the product separation steps. The composition of isomerizer feed is then a function of the virgin $C_8$ aromatic feed, the product separation unit performance, and the isomerizer performance.

It will be apparent that separation techniques for recovery of one or more xylene isomers will not have material effect on the ethylbenzene introduced with charge to the recovery isomerization "loop". That compound, normally present in eight carbon atom aromatic fractions, will accumulate in the loop unless excluded from the charge or converted by some reaction in the loop to products which are separable from xylenes by means tolerable in the loop. Ethylbenzene can be separated from the xylenes of boiling point near that of ethylbenzene by extremely expensive "superfractionation". This capital and operating expense cannot be tolerated in the loop where the high recycle rate would require an extremely large distillation unit for the purpose. It is a usual adjunct of low pressure, low temperature isomerization as a charge preparation facility in which ethylbenzene is separated from the virgin $C_8$ aromatic fraction before introduction to the loop.

Other isomerization processes operate at higher pressure and temperature, usually under hydrogen pressure in the presence of catalysts which convert ethylbenzene to products readily separated by relatively simple distillation in the loop, which distillation is needed in any event to separate by-products of xylene isomerization from the recycle stream. For example, the Octafining catalyst of platinum on silica-alumina composite exhibits the dual functions of hydrogenation/dehydrogenation and isomerization.

The rate of ethylbenzene approach to equilibrium concentration in a $C_8$ aromatic mixture is related to effective contact time. Hydrogen partial pressure has a very significant effect on ethylbenzene approach to equilibrium. Temperature change within the range of Octafining conditions, i.e. 830° F. (443° C.) to 900° F. (482° C.), has but a very small effect on ethylbenzene approach to equilibrium.

Concurrent loss of ethylbenzene to other molecular weight products relates to % approach to equilibrium. Products formed from ethylbenzene include $C_6$+naphthenes, benzene from cracking, benzene and $C_{10}$ aromatics from disproportionation, and total loss to other than $C_8$ molecular weight. $C_5$ and lighter hydrocarbon by-products are also formed.

The three xylenes isomerize much more selectively than does ethylbenzene, but they do exhibit different rates of isomerization and hence, with different feed composition situations the rates of approach to equilibrium vary considerably.

Loss of xylenes to other molecular weight products varies with contact time. By-products include naphthenes, toluene, $C_9$ aromatics and $C_5$ and lighter hydrocracking products.

Ethylbenzene has been found responsible for a relatively rapid decline in catalyst activity and this effect is proportional to its concentration in a $C_8$ aromatic feed mixture. It has been possible to relate catalyst stability (or loss in activity) to feed composition (ethylbenzene constant and hydrogen recycle ratio) so that for any $C_8$ aromatic feed, desired xylene products can be made with a selected suitably long catalyst use cycle.

The utilization of zeolites of the ZSM-5 class, (e.g. ZSM-5, ZSM-12, ZSM-35 and ZSM-38), for xylene isomerization is described in U.S. Pat. Nos. 3,856,871 and 3,856,873.

A significant improvement arose with the introduction of catalysts such as zeolite ZSM-5 combined with a Group VIII metal such as nickel or platinum as described in Morrison U.S. Pat. No. 3,856,872. It is disclosed in this Morrison patent that the catalyst be preferably incorporated in a porous matrix such as alumina. The Group VIII (hydrogenation) metal may then be added after incorporation with the zeolite in a matrix by such means as base exchange or impregnation. In the process of the U.S. Pat. No. 3,856,872 patent, ethylbenzene is converted by disproportionation over this catalyst to benzene and diethylbenzene. At temperatures in excess of 800° F. and using a catalyst comprising a zeolite of the ZSM-5 class and of reduced activity, ethylbenzene and other single ring aromatics are converted by splitting off side chains of two or more carbon atoms as described in copending application Ser. No. 914,645, filed June 12, 1978 now U.S. Pat. No. 4,188,282. A particularly preferred form of zeolite ZSM-5 disclosed in said copending application is formed by the crystallization of the zeolite from a solution containing metal ions, such as platinum. This procedure shall hereinafter be referred to as "co-crystallization".

The use of zeolites characterized by a silica to alumina mole ratio of at least 12 and a Constraint Index in the approximate range of 1 to 12, i.e. the ZSM-5 class of zeolites, in conjunction with a Group VIII metal for aromatics processing, is disclosed in U.S. Pat. Nos. 4,101,595 and 4,101,597. Low pressure xylene isomerization using a zeolite catalyst such as ZSM-5 without a metal function is described in U.S. Pat. No. 4,101,596.

A further improvement in xylene isomerization, as described in U.S. Pat. No. 4,163,028, utilizes a combination of catalyst and operating conditions which decouples ethyl benzene conversion from xylene loss in a xylene isomerization reaction, thus permitting feed of $C_8$ fractions which contain ethyl benzene without sacrifice of xylenes to conditions which will promote adequate conversion of ethyl benzene.

That improved process of the U.S. Pat. No. 4,163,028 patent utilizes a low acid catalyst, typified by zeolite ZSM-5 of low alumina content ($SiO_2/Al_2O_3$ mole ratio of about 500 to 3000 or greater) and which may contain metals such as platinum or nickel. In using this less active catalyst, the temperature is raised to 800° F. (427° C.) or higher for xylene isomerization. At these temperatures, ethylbenzene reacts primarily via dealkylation to benzene and ethylene rather than via disproportionation to benzene and diethylbenzene and hence is strongly decoupled from the catalyst acid function. Since ethylbenzene conversion is less dependent on the acid function, a lower acidity catalyst can be used to perform the relatively easy xylene isomerization, and the amount of xylenes disproportionated is eliminated. The reduction of xylene losses is important because about 75% of the xylene stream is recycled in the loop, resulting in an ultimate xylene loss of 6–10 wt. % by previous processes. Since most of the ethylbenzene goes to benzene instead of benzene plus diethylbenzenes, the product value of the improved process is better than that of prior practices.

SUMMARY OF THE INVENTION

In accordance with the present invention, there has now been discovered novel methods of preparing an aromatics processing catalyst. The catalyst is prepared by incorporating a noble metal, e.g. platinum, in a cationic form with a member or members of the useful zeolites of the invention after crystallization of said zeolite, but prior to final catalyst particle formation. Said useful zeolites are characterized by a silica to alumina mole ratio of at least 12 and a Constraint Index in the approximate range of 1 to 12. A typical preparaton of an aromatics processing catalyst comprises the general steps of zeolite crystallization; mulling with a suitable binder, such as alumina; extrusion to form catalyst particles; and impregnation with an active metal. The conducting of this typical catalyst preparation in accordance with the present invention would entail the impregnation of the zeolite after zeolite crystallization, but prior to extrusion (final catalyst particle formation).

Whereas the prior art discloses incorporation of an active metal, either during zeolite crystallization, i.e. "co-crystallization", or after extrusion, i.e. "post-impregnated extrudate", practicing this invention and thus incorporating the active metal, i.e. nobel metals, after crystallization, but before extrusion, will result in a superior aromatics processing catalyst. The resultant catalyst of the novel methods of the instant invention exhibits improved activity and selectivity as compared to the prior art catalysts.

Catalysts produced by the methods of the present invention are particularly useful in xylene isomerization. The catalysts so produced are even more particularly useful in high temperature xylene isomerization, i.e. xylene isomerizations conducted at temperatures in excess of 800° F. (427° C.).

DESCRIPTION OF PREFERRED EMBODIMENTS

The aromatics processing catalysts produced by the novel method of this invention comprise a member or members of the novel class of zeolites as defined herein, a noble metal and a binder. In practicing the method of the present invention, the noble metal is incorporated with the zeolite subsequent to zeolite crystallization, but prior to extrusion (final catalyst particle formation). Such metal incorporation can be accomplished either before or after the addition of a binder, e.g., mulling with alumina, but in any event, before extrusion. The noble metals include Ru, Rh, Pd, Ag, Os, Ir, Pt and Au.

The zeolite is to be in intimate contact with the moble metal. Such noble metal can be ion exchanged into the zeolite composition, impregnated therein or physically intimately admixed therewith. Such component can be impregnated in or onto the zeolite, such as, for example, by, in the case of the preferred metal, platinum, treating the zeolite with a platinum metal-containing ion. Thus, suitable platinum compounds include various cationic platinum compounds such as platinous chloride and various compounds containing platinum ammine or amine complexes. The amount of noble metal to the amount of total catalyst, i.e. zeolite and binder, can range from between about 0.005 wt. % and about 0.5 wt. %, and preferably from between about 0.05 wt. % and about 0.2 wt. %.

The crystalline zeolites utilized herein are members of a novel class of zeolitic materials which exhibit unusual properties. Although these zeolites have unusually low alumina contents, i.e. high silica to alumina mole ratios, they are very active even when the silica to alumina mole ratio exceeds 30. The activity is surprising, since catalytic activity is generally attributed to framework alumina atoms and/or cations associated with these aluminum atoms. These zeolies retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therfore are conducive to long times on stream between regenerations by burning carbonaceous deposits with oxygen-containing gas such as air.

An important characteristic of the crystal structure of this novel class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratio of at least 12 are useful, it is preferred in some instances to use zeolites having much higher silica to alumina mole ratios, i.e. 1600 and above. In addition, zeolites as otherwise characterized herein but which are substantially free of aluminum, i.e. having silica to alumina mole ratios up to infinity, are found to be useful and even preferable in some instances. Such "high silica" or "highly siliceous" zeolites are intended to be included within this description. Also to be included in this definition are the pure silica analogs of the useful zeolites of this invention, i.e. having absolutely no aluminum (silica to alumina mole ratio of infinity).

The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present invention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1004° F. (540° C.) for at least 15 minutes. The zeolite is then flushed with helium and the temperature is adjusted between 554° F. (290° C.) and 950° F. (510° C.) to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occassionally be necessary to use somewhat more severe conditions for samples of very low activity, such as those having an exceptionally high silica to alumina mole ratio. In those instances, a temperature of up to about 1004° F. (540° C.) and a liquid hourly space velocity of less than one, such as 0.1 or less, can be employed in order to achieve a minimum total conversion of about 10%.

There also may be instances where the activity is so low, e.g. silica to alumina mole ratio approaching infinity, that the Constraint Index cannot be adequately measured, if at all. In such situations, Constraint Index is meant to mean the Constraint Index of the exact same substance, i.e. same crystal structure as determined by such means as X-ray diffraction pattern, but in a measurable form, e.g. high aluminum containing form.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (C.I.) values for some typical materials are:

| | C.I. |
|---|---|
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H-Zeolon (Mordenite) | 0.4 |
| REY | 0.4 |
| Amporphous Silica-Alumina | 0.6 |
| Erionite | 38 |

The above-described Constraint Index is an important and even critical definition of those zeolites which are useful in the instant invention. The very nature of this parameter and the recited technique by which it is determined however, admit of the possiblity that a given zeolite can be tested under somewhat different conditions and thereby exhibit different Constraint indices. Constraint Index seems to vary somewhat with severity of operation (conversion) and the presence or absence of binders. Likewise, other variables such as crystal size of the zeolite, the presence of occluded contaminants, etc., may affect the Constraint Index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The novel class of zeolites defined herein is exemplified by ZSM-5, ZSM-11, ZSM-12, ZSM-23, ZSM-35, ZSM-38, ZSM-48, and other similar materials.

XSM-5 is described in greater detail in U.S. Pat. Nos. 3,702,886 and Re. 29,948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire contents thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 is described in U.S. application Ser. No. 13,640, filed Feb. 21, 1979.

The composition ZSM-48 can be identified, in terms of moles of anhydrous oxides per 100 moles of silica, as follows:

$$(0 \text{ to } 15)RN:(0 \text{ to } 1.5)M_{2/n}O:(0 \text{ to } 2)Al_2O_3:(100)SiO_2$$

wherein M is at least one cation having a valence n, RN is a $C_1$–$C_{20}$ organic compound having at least one amine functional group of $pK_a \leqq 7$, and wherein the composition is characterized by the distinctive X-ray diffraction pattern as shown in Table 1 below.

It is recognized that, particularly when the composition contains tetrahedral, framework aluminum, a fraction of the amine functional groups may be protonated. The doubly protonated form, in conventional notation, would be $(RNH)_2O$ and is equivalent in stoichiometry to $2RN + H_2O$.

The X-ray diffraction pattern of the ZSM-48 has the following significant lines:

TABLE 1

| CHARACTERISTIC LINES OF ZSM-48 | |
|---|---|
| d | Relative Intensity |
| 11.9 | W-S |
| 10.2 | W |
| 7.2 | W |
| 5.9 | W |
| 4.2 | VS |
| 3.9 | VS |
| 3.6 | W |
| 2.85 | W |

These values were determined by standard techniques. The radiation was the K-alpha doublet of copper, and a scintillation counter spectrometer with a strip chart pen recorder was used. The peak heights I, and the positions as a function of 2 times theta, where theta is the Bragg angle, were read from the spectrometer chart. From these, the relative intensities, 100 $I/I_o$, where $I_o$ is the intensity of the strongest line or peak, and d (obs.), the interplanar spacing in A, corresponding to the recorded lines, were calculated. In Table 1 the relaive intensities are given in terms of the symbols W=weak, VS=very strong and W-S=weak-to-strong.Ion exchange of the sodium ion with cations reveals substantially the same pattern with some minor shifts in interplanar spacing and variation in relative intensity. Other minor variations can occur depending on the silicon to aluminum mole ratio of the particular sample, as well as if it has been subjected to thermal treatment.

ZSM-48 can be prepared from a reaction mixture containing a source of silica, RN, an alkali metal oxide, e.g. sodium, water, and optionally alumina, and having a composition, in terms of mole ratios of oxides, falling within the following ranges:

| REACTANTS | | BROAD | PREFERRED |
|---|---|---|---|
| $Al_2O_3/SiO_2$ | = | 0 to 0.02 | 0 to 0.01 |
| $Na/SiO_2$ | = | 0 to 2 | 0.1 to 1.0 |
| $RN/SiO_2$ | = | 0.01 to 2.0 | 0.05 to 1.0 |
| $OH^-/SiO_2$ | = | 0 to 0.25 | 0 to 0.1 |
| $H_2O/SiO_2$ | = | 10 to 100 | 20 to 70 |
| H + (added)/$SiO_2$ | = | 0 to 0.2 | 0 to 0.05 |

wherein RN is a $C_1$–$C_{20}$ organic compound having amine functional group of $pK_a \leqq 7$, and maintaining the mixture at 80°–250° C. until crystals of ZSM-48 are formed. H+(added) is moles acid added in excess of the moles of hydroxide added. In calculating H+(added) and OH values, the term acid (H+) includes both hydronium ion, whether free or coordinated, and aluminum. Thus aluminum sulfate, for example, would be considered a mixture of aluminum oxide, sulfuric acid, and water. An amine hydrochloride would be a mixture of amine and HCl. In preparing the highly siliceous form of ZSM-48, no alumina is added. The only aluminum present occurs as an impurity.

Preferably, crystallization is carried out under pressure in an autoclave or static bomb reactor, at 176° F. (80° C.) to 482° F. (250° C.). Thereafter, the crystals are separated from the liquid and recovered. The composition can be prepared utilizing materials which supply the appropriate oxide. Such compositions include sodium silicate, silica hydrosol, silica gel, silicic acid, RN, sodium hydroxide, sodium chloride, aluminum sulfate, sodium aluminate, aluminum oxide, or aluminum itself. RN is a $C_1$–$C_{20}$ organic compound containing at least one amine functional group of $pK_a \leqq 7$ and includes such compounds as $C_3$–$C_{18}$ primary, secondary, and tertiary amines, cyclic amine, such as piperidine, pyrrolidine and piperazine, and polyamines such as $NH_2$—$C_nH_{2n}$—$NH_2$ wherein n is 4–12.

It is to be understood that by incorporating by reference the foregoing patents to describe examples of specific members of the novel class with greater particularly, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intracrystalline free space is occupied by organic cations from the forming solution. They may be activated by heating in an inert atmosphere at 1004° F. (540° C.) for one hour, for example, followed by base exchange with ammonium salts followed by calcination at 1004° F. (540° C.) in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 1004° F. (540° C.) for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38 and ZSM-48, with ZSM-5 being particularly preferred.

In a preferred aspect of this invention, the zeolites hereof are selected as those providing among other things a crystal framework density, in the dry hydrogen form, of not less than about 100 lbs. per cubic foot (1.6 grams per cubic centimeter). It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article ZEOLITE STRUCTURE by W. M. Meier. This paper, the entire contents of which are incorporated herein by reference, is included in PROCEEDINGS OF THE CONFERENCE ON MOLECULAR SIEVES (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

| | Void Volume cc/cc | Framework Density g/cc | lb/ft³ |
|---|---|---|---|
| Ferrierite | 0.28 | 1.76 | 109.9 |

-continued

| | Void Volume cc/cc | Framework Density g/cc | lb/ft$^3$ |
|---|---|---|---|
| Mordenite | .28 | 1.7 | 106.1 |
| ZSM-5, -11 | .29 | 1.79 | 111.7 |
| ZSM-12 | — | 1.8 | 112.4 |
| ZSM-23 | — | 2.0 | 124.9 |
| Dachiardite | .32 | 1.72 | 107.4 |
| L | .32 | 1.61 | 100.5 |
| Clinoptilolite | .34 | 1.71 | 106.8 |
| Laumontite | .34 | 1.77 | 110.5 |
| ZSM-4 (Omega) | .38 | 1.65 | 103.0 |
| Heulandite | .39 | 1.69 | 105.5 |
| P | .41 | 1.57 | 98.0 |
| Offretite | .40 | 1.55 | 96.8 |
| Levynite | .40 | 1.54 | 96.2 |
| Erionite | .35 | 1.51 | 94.3 |
| Gmelinite | .44 | 1.46 | 91.2 |
| Chabazite | .47 | 1.45 | 90.5 |
| A | .5 | 1.3 | 81.1 |
| Y | .48 | 1.27 | 79.2 |

When synthesized in the alkali metal form, the zeolite can be conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used.

As is the case of many catalysts, it is desired to incorporate the zeolite with another material resistant to the temperatures and other conditions employed in organic conversion processes. Such materials include active and inactive materials as well as inorganic material such as clays, silica and/or metal oxides. Inactive materials suitably serve as diluents to control the amount of conversion in a given process to that products can be obtained economically and orderly without employing other means for controlling the ratio of reaction.

Binders useful for compositing with the useful zeolite herein also include inroganic oxides, notably alumina, which is particularly preferred.

In addition to the foregoing materials, the zeolite catalyst can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The relative proportions of finely divided crystalline zeolite and inorganic oxide matrix vary widely with the zeolite content ranging from about 1 to about 90 percent by weight and more usually in the range of about 2 to about 50 percent by weight of the composite.

It may be preferred to use a catalyst of controlled acid activity in many processes and process conditions embraced by the present invention. This controlled acid activity of the catalyst is attainable in any of several ways or a combination of these. A preferred method to reduce activity is to form the zeolite at high silica to alumina mole ratio above 200, preferably above 500. Very high dilution with an inert matrix is also effective.- For example, composites of a more active form of zeolite ZSM-5 with alumina at a ratio of 5 parts of zeolite with 95 parts of the inert matrix provide a suitable catalyst as described in U.S. Pat. No. 4,152,363, the entire contents of which are incorporated herein by reference.

Activity of these zeolites may also be reduced by thermal treatment or steam at high temperature as described in U.S. Pat. Nos. 3,965,209 and 4,016,218, the entire contents of which are incorporated by reference herein. Zeolites employed in such severe reactions as aromatization of paraffins and olefins lose activity to an extent which makes them suitable for use in the process of this invention. See U.S. Pat. No. 3,960,978 for fuller discussion of this manner of deactivated zeolite, the entire contents of which are incorporated by reference herein. Another method for reducing activity is to provide basic cations such as sodium at a significant proportion of the cationic sites of the zeolite. That technique is described in U.S. Pat. No. 3,899,544, the entire contents of which are incorporated by reference herein.

By whatever means the controlled acid activity is achieved, the activity may be measured in terms of disproportionation activity. A suitable test for this purpose involves contacting xylenes in any convenient mixture or as a single pure isomer over the catalyst at 900° F. (482° C.), 200 psig (1480 kPa) and liquid hourly space velocity (LHSV) of 5. Suitable catalysts for use in the process of this invention will show a single pass loss of xylenes (by disproportionation) of less than 2 weight percent, preferably less than one percent. Catalysts which have been employed show losses in the neighborhood of 0.5 percent. Itis this very low rate of disproportionation at very high levels of ethyl benzene conversion to benzene (about 30%) that provides the advantage of the new chemistry of aromatics processing characteristic of this invention. That lack of disproportionation (and transalkylation generally) activity also dictates withdrawal of compounds boiling above and below eight carbon atom aromatic compounds. For example, toluene and trimethyl benzene are converted to very little, if any, extent and become diluents which occupy reactor space to no advantage. Small amounts of such diluents can be tolerated, such as those present by reason of "sloppy" fractionation, but withdrawal to at least a major extent is important to efficient operation.

A preferred procedure for preparing a typical Pt-ZSM-5/$Al_2O_3$ composite catalyst according to the instant invention would comprise the following steps:

(1) preparing ZSM-5 by known procedures
(2) mulling the ZSM-5 with an alumina binder and water to form an extrudable mass
(3) contacting the extrudable mass of ZSM-5 and alumina binder with an aqueous platinum-containing solution such as tetraamine platinum (II) chloride
(4) extruding the Pt-ZSM-5/$Al_2O_3$ to form catalyst pellets, followed by drying
(5) calcining in nitrogen to decompose the organics in the ZSM-5
(6) base-exchanging with ammonium ion solution to remove sodium from the ZSM-5
(7) drying
(8) calcining in air
(9) steam treating the final catalyst particles at about 1025° F. (552° C.).

Table 2 immediately set forth hereinbelow compares the step-wise preparation of Pt-ZSM-5/$Al_2O_3$ composite catalyst by two conventional methods, i.e. "post-impregnation" and "co-crystallization", and by two methods of the instant invention, side by side, i.e. zeolite impregnation and composite impregnation.

TABLE 2

| PREPARATION OF A Pt—ZSM-5/$Al_2O_3$ CATALYST Conventional Preparation Methods | |
|---|---|
| Post-Impregnation | Co-Crystallization |
| 1. Crystallization of ZSM-5 | 1. Crystallization of ZSM-5 with Pt |
| 2. Mulling with $Al_2O_3$ binder | 2. Mulling with $Al_2O_3$ binder |
| 3. Extrusion of ZSM-5/$Al_2O_3$ into catalyst pellets | 3. Extrusion of Pt—ZSM-5/$Al_2O_3$ into catalyst pellets |
| 4. Drying | 4. Drying |
| 5. Calcining in $N_2$ | 5. Calcining in $N_2$ |
| 6. Base-exchange with ammonium ions | 6. Base-exchange with ammonium ions |
| 7. Drying | 7. Drying |
| 8. Impregnation of ZSM-5/$Al_2O_3$ with Pt | 8. Calcining in air |
| 9. Calcining in air | *9. Steam treatment |
| *10. Steam treatment | |

| PREPARATION OF A Pt—ZSM-5/$Al_2O_3$ CATALYST New Methods of this Invention | |
|---|---|
| Composite Impregnation | Zeolite Impregnation |
| 1. Crystallization of ZSM-5 | 1. Crystallization of ZSM-5 |
| 2. Mulling the ZSM-5 with $Al_2O_3$ binder | 2. Impregnation of ZSM-5 with Pt |
| 3. Impregnation of the ZSM-5/$Al_2O_3$ with Pt | 3. Mulling Pt—ZSM-5 with $Al_2O_3$ binder |
| 4. Extrusion of Pt—ZSM-5/$Al_2O_3$ into catalyst pellets | 4. Extrusion of Pt ZSM-5/$Al_2O_3$ into catalyst pellets |
| 5. Drying | 5. Drying |
| 6. Calcining in $N_2$ and/or air | 6. Calcining in $N_2$ and/or air |
| 7. Base-exchange with ammonium ions | 7. Base exchange with ammonium ions |
| 8. Drying | 8. Drying |
| 9. Calcining in air | 9. Calcining in air |
| *10. Steam treatment | *10. Steam treatment |

*Steam treatment is optional depending on silica/alumina mole ratio of the zeolite (ZSM-5 in these preparations).

As can be seen, the preferred method of preparing Pt-ZSM-5/$Al_2O_3$ catalyst distinctly differs from the prior art methods of manufacturing the catalyst. Indeed, the method of the present invention produces a catalyst with better metal distribution than the prior art methods. Also the catalyst produced by the method of this invention shows little or no aging in comparison with the prior art produced catalysts.

Catalysts produced by the method of this invention offer the following additional advantages:

The improved catalytic activity for paraffin and ethyl benzene conversions may allow for processing unextracted feedstocks, thus reducing extensive separation/-distillation costs for fractionally separating paraffins from xylene/ethyl benzene feeds.

The precalcination step that removes the organics (introduced during zeolite crystallization) fixes the noble metal on the zeolite (or zeolite + $Al_2O_3$), rendering it impervious to base exchange. Thus ion exchange of ammonium (hydrogen) for sodium may be done in the presence of the affixed platinum. With the typical Ni on HZSM-5 catalyst, nickel must be added (exchanged) at the end of the catalyst procedure. With the catalyst produced by the method of this invention, it is feasible to back-exchange various amounts of other metals such as Ni, Cu, etc., to produce various noble metal combinations without losing noble metal.

The catalyst manufacturing process is simplified (especially compared with prior co-crystallized catalysts) in that existing equipment may be used with only slight modification in procedures.

The catalyst prepared according to the novel method of the present invention is particularly useful in aromatics processing and most particularly for xylene isomerization processes such as the one described in U.S. Pat. No. 4,163,028, the entire contents of which are incorporated herein by reference.

Conditions for conducting such xylene isomerizations with the catalyst produced according to the method of the present invention include a temperature of between about 500° F. (260° C.) and 1000° F. (540° C.) and preferably between aout 800° F. (430° C.) and about 900° F. (490° C.); a pressure of between about 50 psig (450 kPa) and about 1000 psig (7000 kPa), preferably from between about 100 psig (700 kPa) and about 400 psig (2860 kPa); and a weight hourly space velocity of between about 1 and about 50 and preferably between about 5 and about 15. It is preferred to conduct xylene isomerization in accordance with this invention in the presence of hydrogen. If hydrogen is used, the hydrogen/hydrocarbon mole ratio is between about 1 and 20 preferably between about 3 and 8.

The specific examples, hereinafter discussed, will serve to illustrate the present invention, without unduly limiting same.

EXAMPLE 1

This example illustrates the preparation of a Pt-ZSM-5/$Al_2O_3$ catalyst according to a novel method of this invention wherein the ZSM-5 was in a highly siliceous form and the platinum level of the finished catalyst was 0.2 wt. %. In this example, the ZSM-5 and alumina were mulled into a composite and then impregnated with platinum, i.e. composite impregnation.

A sodium silicate solution was prepared by mixing 36.62 parts of sodium silicate (28.7 wt. % $SiO_2$, 8.9 wt. % $Na_2O$, 21.17 parts water and 0.11 parts Daxad 27 (W. R. Grace & Company).

An acid solution was prepared by adding together 3.83 parts $H_2SO_4$, 4.33 parts NaCl and 21.73 parts water.

The sodium silicate solution and acid solution were mixed in a stirred autoclave containing 1.05 parts water. Added to this mixed solution was 2.52 parts NaCl to form a gel.

An organic solution was prepared by adding together 2.46 parts tri-n-propylamine. 2.12 parts n-propylbromide and 4.07 parts methylethylketone.

The organic solution was added to the gel and the resultant mixture was heated to 210° F. (100° C.). After crystallization was greater than about 50% complete, the temperature was increased to 320° F. (160° C.) for 8 hours. Unreacted organics were removed by flashing and the remaining contents were cooled. The remaining zeolite was dialyzed, dried and identified as ZSM-5 having a silica to alumina mole ratio of about 520.

A mixture of 49.82 parts of the above formed ZSM-5 zeolite and 49.82 parts dried alumina was treated in a muller with a solution containing 0.36 parts tetraamine platinum (II) chloride and with sufficient water to extrudate the mass into 1/16 inch (0.16 cm) pellets. The extruded material contained 50 parts ZSM-5, 50 parts alumina and about 0.2 wt. % platinum.

The dried extrudate was calcined for 2.2 hours in flowing nitrogen at 1000° F. (540° C.). After slowly cooling under nitrogen, the extrudate was contacted with an ammonium nitrate exchange solution (containing about 0.4 lbs. $NH_4NO_3$/lb. extrudate) at ambient temperature until the sodium level was reduced to below 0.1%. After said exchange, the extrudate was washed, dried and calcined in air at 1000° F. (540° C.) for 3 hours. The resultant catalyst composite was then heated in air to about 975° F. (530° C.) and steam was gradually introduced into the reactor tube. When 100% steam was attained, the temperature was adjusted to 1025° F. (550° C.) and held constant for 3 hours. The catalyst was then cooled in nitrogen.

EXAMPLE 2

The same procedure utilized in Example 1 was performed in this example, with the exception that one-half the amount of tetraamine platinum (II) chloride was used. The resultant catalyst extrudate contained 0.11 wt. % platinum.

EXAMPLE 3

The same procedure employed in Example 1 was conducted in this example, with the exception that one-fourth the amount of tetraamine platinum (II) chloride was used. The resultant catalyst extrudate contained 0.05 wt. % platinum.

EXAMPLE 4

This example illustrates the preparation of a Pt-ZSM-5/$Al_2O_3$ catalyst according to a novel method of this invention wherein the ZSM-5 is in a highly siliceous form. Whereas the catalyst prepared according to Examples 1-3 was composite impregnated, the catalyst prepared according to this example was zeolite impregnated.

The procedure of Example 1 was followed with the following exception: the dried zeolite was contacted with a solution of tetraamine platinum (II) chloride before addition of the alumina. After such contact, the alumina was added to the muller before extrusion and the same remaining procedure as given in Example 1 was carried out.

EXAMPLE 5

This example illustrates the preparation of a Pt-ZSM-5/$Al_2O_3$ catalyst according to a novel method of the instant invention. In this example, the ZSM-5 had a lower silica to alumina mole ratio than that used in Examples 1-4, namely, a $SiO_2/Al_2O_3$ mole ratio of about 70. The mode of impregnation employed in this example was composite impregnation.

A sodium silicate solution was prepared by mixing 16 parts water and 27.7 parts sodium silicate (28.7 wt. % $SiO_2$, 8.9 wt. % $Na_2O$, 62.4%, $H_2O$) followed by addition of 0.08 parts Daxad 27 (W. R. Grace & Company). The solution was cooled to approximately 60° F. (15° C.).

An acid solution was prepared by adding 1 part aluminum sulfate (17.2 wt. % $Al_2O_3$) to 16.4 parts water followed by 2.4 parts sulfuric acid (93 wt. % $H_2SO_4$) and 1.2 parts NaCl.

These solutions were mixed in an agitated vessel. A total of 5.1 parts of NaCl were added to the acid solution and gel. The gel molar ratios expressed as oxides are the following:

$SiO_2/Al_2O_3 = 78.4$ $Na_2O/Al_2O_3 = 49.9$

An organic solution was prepared by adding 1.6 parts n-propyl bromide and 3.1 parts methyl ethyl ketone to 1.9 parts tri-n-propylamine.

After the gel was heated to about 200° F. (95° C.), agitation was reduced and the organic solution was added above the gel. This mixture was held at about 200°-230° F. (95°-110° C.) for 14 hours, then severe agitation was resumed. When approximately 65% of the gel as crystallized, the temperature was increased to 300°-320° F. (150°-160° C.) and held there until crystallization was complete. Unreacted organics were removed by flashing and the remaining contents cooled.

The zeolite slurry product was diluted with 4-5 parts water per part slurry and 0.0002 parts of flocculent (Rohm & Haas Primafloc C-7) per part slurry, allowed to settle and supernatant liquid was drawn off. The settled solids were reslurried to the original volume of the preceding step with water and 0.00005 part of flocculant per part slurry. After settling, the aqueous phase was decanted. This procedure was repeated until the sodium level of the zeolite was less than 1.0 wt. %. The washed zeolite was then filtered, dried and identified as ZSM-5 having a silica/alumina mole ratio of at least 12, i.e., about 70, and a constraint index of between about 1 and 12, i.e. about 8.3.

A mixture of 49.91 parts of dried ZSM-5 zeolite and 49.91 parts dried alumina was contacted in a muller with a solution containing 0.18 parts tetraamine platinum (II) chloride and with a sufficient amount of water to form 1/16 inch (0.16 cm) pellets. The extruded material contained 50 parts ZSM-5 zeolite, 50 parts alumina and 0.1 wt. % platinum.

The extrudate was dried and calcined in nitrogen for 3 hours. The calcined extrudate was then exchanged with ammonium nitrate solution (containing about 0.4 lbs $NH_4NO_3$/lb. extrudate) which reduced the sodium content below 0.05%. The exchanged extrudate was washed, dried and calcined in air at 1000° F. (540° C.) for 3 hours. The catalyst was then steamed (100% steam) at 1025° F. (550° C.) for 24-26 hours.

TABLE 3

COMPARISON OF VARIOUS AROMATICS PROCESSING CATALYSTS

| Example No. | 7 | 8 | 9 | 10 | 11 | 12 |
|---|---|---|---|---|---|---|
| Catalyst Type | Composite Impregnated Pt—ZSM-5/alumina (high silica/alumina mole ratio) | Ni—ZSM-5 | Pure ZSM-5 cc Pt | ZSM-5 cc Pt Extrudate | Post-Impregnated | Bulk Diluted |
| Temperature, °F. | 871 | 626 | 899 | 873 | 899 | 902 |
| EB Conversion, % | 65.2 | 36.0 | 35.0 | 52.0 | 56.6 | 50.5 |
| Xylene Loss, % | 1.4 | 5.2 | 0.2 | 1.0 | 1.0 | 0.6 |
| Ring Loss, % | 0.9 | −0.2 | 0.3 | 0.5 | 0.3 | 0.6 |
| n-$C_9$ Comversion, % | 91.7 | 98.0 | 61.9 | 63.5 | 70.5 | 78.2 |
| i-$C_8$ Conversion, % | 28.0 | 13.6 | 12.8 | 25.9 | 13.9 | 29.7 |
| $C_6H_6/\Delta EB$ (moles) | 0.77 | 0.40 | 0.81 | 0.83 | 0.79 | 0.82 |
| $C_2/\Delta EB$ | 0.89 | 0 | 0.92 | 0.96 | 0.85 | 0.90 |
| $C_2^=/C_2$ | 0.08 | 0 | 0.12 | 0.09 | 0.1 | 0.09 |
| p-Xyl/(p-Xyl)eq. % | 105 | 105 | 101 | 105 | 105 | 106 |
| Pt, ppm | 2000 (0.2% Pt on total catalyst) | 9400(Ni) | 7600 | 1400 | 2000 | 75 |

EXAMPLE 6

In this example, the same procedure as used in Example 5 was conducted, with the following exception: the dried zeolite was contacted with the platinum containing solution before addition of the alumina. The alumina was added to the muller and the contents were extruded forming 1/16 inch (0.16 cm) pellets. The remaining procedure of Example 5 was followed resulting in a zeolite impregnated catalyst containing 0.1% Pt. and 0.03% sodium.

EXAMPLES 7-12

The composite impregnated high silica/alumina ZSM-5 with 0.2 wt. % Pt catalyst prepared according to Example 1 was compared against various conventional catalysts in Examples 7-12. The results for this comparison are given in Table 3. All the catalysts used in Examples 7-12 were in contact with the following chargestock:

| | |
|---|---|
| Ethylbenzene | 14% |
| p-Xylene | 9% |
| m-Xylene | 65% |
| o-Xylene | 6% |
| i-$C_8H_{18}$ | 3% |
| n-$C_9H_{20}$ | 3% |

The catalysts used in Examples 7-12 were contacted with the aforesaid chargestock at the following reaction conditions:

| | |
|---|---|
| WHSV | 6.8 |
| $H_2$/HC | 6.5-7 |
| Pressure | 200 psig (1480 kPa) |
| Temperature | 600-900° F. (316-482° C.) |

The catalyst utilized in Example 7 represents a catalyst prepared according to one of the improved methods of this invention and prepared according to the general procedure of Example 1.

The catalyst employed in Example 8 was a conventional commercial aromatics processing catalyst, namely Ni-ZSM-5/$Al_2O_3$ containing 0.94% Ni. The catalyst of Example 9 was pure ZSM-5 co-crystallized with platinum (ZSM-5 cc Pt) containing 0.76% Pt and with the ZSM-5 having a silica to alumina mole ratio of 1040. A bound extrudate version of the catalyst of Example 9 was used in Example 10. This catalyst had a zeolite to alumina binder ratio of 35/65 and a platinum content of 0.14%. In Example 11, a post-impregnated extrudate catalyst was employed. This catalyst contained ZSM-5 with a 70/1 silica to alumina mole ratio and was steamed for 16 hours at 1050° F. to control zeolite activity. In Example 12, a bulk diluted HZSM-5 extrudate impregnated to contain 75 ppm Pt and 1 wt. % ZSM-5 (99% alumina) was utilized.

The superior catalytic properties (activity and selectivity) of the catalyst prepared according to one of the methods of this invention are clearly demonstrated in comparison with other catalysts in Table 3. The highest ethylbenzene (EB) conversion (65.2%) was attained with the catalyst produced by the instant invention. This catalyst also demonstrated very good selectivity with a xylene loss of less than 1.5%. The catalyst prepared according to one of the novel methods of this invention also showed very good activity for paraffin conversion. In comparison with all the other platinum-containing catalysts of Table 3, the catalyst prepared according to Example 1 gave the best conversion of n-$C_9$. The fact that this catalyst demonstrates high activity for paraffin conversion would be significant in processing unextracted feedstocks, e.g. $C_8$ reformate cuts which contain paraffins and naphthenes.

EXAMPLE 13

The composite impregnated, high silica/alumina ZSM-5 with 0.11 wt. % Pt catalyst prepared according to Example 2 was contacted with an ethylbenzenexylene-paraffin feed at the following conditions:

| | |
|---|---|
| WHSV | 7 and 13.7 |
| $H_2$/HC | about 7 |
| Pressure | 200 psig (1480 kPa) |
| Temperature | 877° F. (470° C.) |

The feedstock composition was as follows:

| | |
|---|---|
| Ethylbenzene | 14% |
| p-Xylene | 12% |
| m-Xylene | 62% |
| o-Xylene | 6% |
| i-$C_8H_{18}$ | 3% |
| n-$C_9H_{20}$ | 3% |

The results of this example are given below in Table 4.

TABLE 4

| | | |
|---|---|---|
| Temperature, °F. | 877 | 877 |
| WHSV | 7.0 | 13.7 |
| EB Conversion, % | 64.8 | 41.6 |
| Xylene Loss, % | 1.3 | 0.55 |
| Ring Loss, % | 0.9 | 0.3 |
| n-$C_9$ Conversion, % | 79.15 | 49.1 |
| i-$C_8$ Conversion, % | 27.8 | 18.4 |
| $C_6H_6/\Delta EB$ (Moles) | 0.74 | 0.79 |
| $C_2/\Delta EB$ | 0.88 | 0.87 |
| $C_2^=/C_2$ | 0.07 | 0.13 |
| p-Xyl/(p-Xyl)eq. % | 105 | 105 |
| ppm Pt | 1000 | 1000 |

EXAMPLES 14–15

These examples illustrate the effects of steaming low silica/alumina mole ratio zeolite catalyst prepared according to this invention. The feedstock utilized in these examples was the same as that given previously in Example 13. The catalysts employed in these examples were prepared according to Example 5. The results for these examples are given in Table 5.

TABLE 5

| | Example 14 | Example 15 |
|---|---|---|
| Catalyst Preparation | Steamed at 1025° C. for 36 hours | Not steamed |
| Reaction Conditions | | |
| Temperature, °F. | 871 | 870 |
| WHSV | 6.8 | 6.9 |
| Pressure, psig | 200 | 200 |
| $H_2$/HC | 5.6 | 5.6 |
| Conversions and Losses: | | |
| EB Conv., % | 63.5 | 98.3 |
| n-$C_9$ Conv., % | 59.7 | 99.5 |
| i-$C_8$ Conv., % | 17.0 | 53.1 |
| Xylene Loss, % | 1.6 | 26.1 |
| Ring Loss, % | 0.3 | 3.7 |
| p-Xyl/(p-Xyl)eq. % | 104.9 | 105.2 |

It is evident from the above that steaming is preferred for a low silica/alumina mole ratio zeolite containing catalyst to drastically reduce both xylene and ring losses.

EXAMPLES 16–17

These examples illustrate the effects of steaming on high silica/alumina mole ratio zeolite catalysts prepared according to this invention. The feedstock utilized for these examples was the same as that given previously in Example 13. The catalysts employed in these examples were prepared according to the general procedure of Example 1, with the exception that steaming step was in accordance with that given below in Table 6. The results for these examples are given in Table 6.

TABLE 6

| | Example 16 | Example 17 |
|---|---|---|
| Catalyst Preparations | Steamed at 1025° F. for 3 Hours | Unsteamed |
| Reaction Conditions: | | |
| Temperature, °F. | 871° F. | 870° F. |
| WHSV | 6.9 | 6.7 |
| Pressure, psig | 200 | 200 |
| $H_2$HC (approx.) | 7 | 7 |
| Conversions and Losses: | | |
| EB Conversion, % | 66.0 | 54.9 |
| Xylene Loss, % | 1.8 | 2.1 |
| Ring Loss, % | 1.3 | 1.9 |
| n-$C_9$ Conversion, % | 93.2 | 99.5 |
| i-$C_8$ Conversion, % | 30.3 | 47.4 |
| $C_6H_6/\Delta EB$ (Moles) | 0.76 | 0.73 |

TABLE 6-continued

| | Example 16 | Example 17 |
|---|---|---|
| $C_2/\Delta EB$ | 0.87 | 0.81 |
| $C_2^=/C_2$ | 0.08 | 0.05 |
| p-Xyl/(p-Xyl)eq. % | 104.7 | 104.7 |

From studying the above, it is noticed that for high silica/alumina mole ratio zeolite catalysts, steaming increases the activity for EB conversion, while slightly decreasing xylene and ring losses and also reducing activity for paraffin conversion.

What is claimed is:

1. A method for preparing a noble metal-containing zeolite catalyst which comprises incorporating a noble metal in a cationic form with a zeolite after crystallization of the zeolite, prior to final catalyst particle formation and prior to any calcination or steaming of said zeolite, said zeolite being characterized by a silica to alumina mole ratio of at least 12 and a Constraint Index in the approximate range of 1 to 12.

2. The method of claim 1 wherein said noble metal is one or more members selected from the group consisting of ruthenium, rhodium, palladium, silver, osmium, iridium, platinum and gold.

3. The method of claim 2 wherein said noble metal is platinum.

4. The method of claim 1 wherein said zeolite is one or more members selected from the group consisting of ZSM-5, ZSM-11, ZSM-12, ZSM-23, ZSM-35, ZSM-38 and ZSM-48.

5. The method of claim 4 wherein said zeolite is ZSM-5.

6. The method of claim 1 wherein incorporating said noble metal with said zeolite occurs via ion exchange.

7. The method of claim 1 wherein incorporating said noble metal with said zeolite occurs via impregnation.

8. The method of claim 1 wherein incorporating said noble metal with said zeolite occurs via physical intimate admixing.

9. The method of claim 1 wherein the noble metal content ranges from between about 0.005 wt. % and about 0.5 wt. % of total catalyst.

10. The method of claim 9 wherein the noble metal content ranges from between about 0.05 wt. % and about 0.20 wt. % of total catalyst.

11. The method of claim 1 wherein said zeolite is mulled with a binder before said incorporation with the noble metal, but prior to final catalyst particle formation.

12. The method of claim 1 wherein a binder is added after incorporating the noble metal with the zeolite, but prior to final catalyst particle formation.

13. The method of claim 11 wherein said binder is alumina.

14. The method of claim 12 wherein said binder is alumina.

15. The method of claim 1 wherein said catalyst is of controlled acid activity.

16. The method of claim 15 wherein said controlled acid activity is achieved by utilizing a zeolite with a high silica to alumina mole ratio.

17. The method of claim 16 wherein said high silica to alumina mole ratio is above 200.

18. The method of claim 17 wherein said high silica to alumina mole ratio is above 500.

19. The method of claim 15 wherein said controlled acid activity is achieved by steam treatment of the catalyst.

20. The method of claim 15 wherein said controlled acid activity is achieved by utilizing a zeolite having a significant proportion of its cationic sites occupied by basic cations.

21. The method of claim 20 wherein said basic cations are sodium cations.

22. The method of claim 15 wherein said controlled acid activity is achieved by utilizing a zeolite with a high silica to alumina mole ratio in combination with steam treatment of the catalyst.

23. The method of claim 22 wherein said high silica to alumina mole ratio is above 200.

24. The method of claim 23 wherein said high silica to alumina mole ratio is above 500.

25. The catalyst produced by the method of claim 1, 2, 3, 4, 5, 6, 7, 8, 9, 10, 11, 12, 13, 14, 15, 16, 17, 18, 19, 20, 21, 22, 23 or 24.

*26. An improved method for preparing a composite zeolite-alumina catalyst wherein a crystalline zeolite having a silica to alumina mole ratio of at least 200 and a Constraint Index of about 1 to 12 has controlled acid activity by utilizing said zeolite in combination with alumina binder and steam treatment at elevated temperature;*

*which comprises incorporating a noble metal in a cationic form with the zeolite after crystallization of the zeolite, prior to final composite catalyst formation and prior to any calcination or steaming of the zeolite.*

*27. In the method for preparing a composite zeolite-alumina catalyst according to claim 26, the further improvement wherein said noble metal consists essentially of platinum and wherein said zeolite consists essentially of acid ZSM-5 and wherein said zeolite noble metal and alumina are intimately mixed by mulling prior to final composite catalyst particle formation.*

*28. In the method for preparing a composite zeolite-alumina catalyst according to claim 27, the further improvement wherein said zeolite mole ratio is about 500 and platinum content ranges between about 0.005 wt. % and about 0.05 wt. % of total catalyst.*

*29. In the method for preparing a composite zeolite-alumina catalyst wherein a crystalline zeolite having a silica to alumina mole ratio of at least 200 and a Constraint Index of about 1 to 12 has controlled acid activity by utilizing said zeolite in combination with alumina binder and steam treatment at elevated temperature; the improvement which comprises mulling alumina binder with the zeolite and water to form an extrudable mass; forming the composite catalyst by extrusion of the zeolite-alumina mixture, calcining the extrudate composite, and steam treating the calcined composite.*

*30. In the method for preparing a composite zeolite-alumina catalyst according to claim 29, the further improvement wherein acid ZSM-5 zeolite is incorporated with about 0.005 wt. % to 0.5 wt. % platinum prior to final composite catalyst formation and prior to any calcination of the zeolite.*

*31. A catalyst produced by the method of claim 26, 27, 28, 29 or 30.*

* * * * *